United States Patent [19]
Klosterman

[11] Patent Number: 5,443,081
[45] Date of Patent: Aug. 22, 1995

[54] GUIDEWIRE CONTAINMENT APPARATUS AND METHOD

[75] Inventor: James J. Klosterman, Waconia, Minn.

[73] Assignee: Lake Region Manufacturing Co., Inc., Chaska, Minn.

[21] Appl. No.: 177,265

[22] Filed: Jan. 4, 1994

Related U.S. Application Data

[63] Continuation of Ser. No. 787,068, Nov. 14, 1991, Pat. No. 5,279,573.

[51] Int. Cl.$^6$ ................................................ A61B 5/00
[52] U.S. Cl. ...................................... 128/772; 222/525; 206/438
[58] Field of Search ................. 128/772, 657; 604/164, 604/171, 280, 166, 163, 158, 160, 161, 283; 206/438, 63.3, 53, 403, 404, 409; 242/129, 77.5, 85, 96, 99, 170, 171; 222/499, 522, 525, 575

[56] References Cited

U.S. PATENT DOCUMENTS

| | | | |
|---|---|---|---|
| 5,125,416 | 6/1992 | Phillips | 128/772 |
| 5,125,905 | 6/1992 | Wright et al. | 604/171 |
| 5,273,042 | 12/1993 | Lynch et al. | 128/657 |
| 5,282,479 | 2/1994 | Havran | 128/772 |

*Primary Examiner*—Stephen C. Pellegrino
*Assistant Examiner*—Guy Tucker
*Attorney, Agent, or Firm*—Grady J. Frenchick

[57] ABSTRACT

A wire containing or dispensing article and method are disclosed. The invention is used to dispense wire from a tubular wire carrier. The invention is particularly useful for containing/dispensing a guidewire, especially a coated guidewire. The article is an elongate dispensing sleeve or collar having an axial hole or bore through which a wire may pass. The sleeve has a cylindrical sleeve body with lateral projections on its outside and a plurality of transverse slits passing through its wall. The lateral projections and slits cooperate to permit wire to be restrictively engaged at the bore and to be controllably dispensed from the carrier by the partial insertion and removal of the sleeve into and out of the carrier. The method is controllable dispensing of the wire from the carrier by utilization of the article.

9 Claims, 6 Drawing Sheets

GUIDEWIRE CONTAINMENT APPARATUS AND METHOD

This is a divisional of application Ser. No. 07/787,068 filed on Nov. 4, 1992 now U.S. Pat. No. 5,279,573.

BACKGROUND OF THE INVENTION

This invention relates to devices, or apparatuses for dispensing wire from substantially cylindrical or tubular containment structure. This invention also relates to wire containing or transporting apparatuses or carriers where the wire has a tendency to migrate from the apparatus during shipping or handling. More particularly, in a preferred practice, the present invention relates to apparatuses and methods for containing and dispensing a specific type of wire namely, a guidewire. This invention is particularly applicable to the process of guidewire containment in dispenser assemblies where the guidewire has a slippery coating thereon.

Guidewires have been described in a number of patents, representative examples of which are U.S. Pat. No. 4,545,390 to Leary, U.S. Pat. No. 3,973,556 to Fleischhacker et al., and U.S. Pat. No. 4,538,622 to Samson et al. Guidewires have many different structural features and configurations depending upon the medical procedure with which they are to be used. Generally speaking, guidewires are used in the process of directing a catheter to identified locations or sites within a patient's cardiovascular or peripheral vascular system for the purpose of diagnosis or treatment. Typically, the guidewire is placed percutaneously into a patient's blood vessel and is directed to the previously identified site. A catheter selected to provide the particular medical procedure at the site then is advanced over the guidewire until the functional structure, working or operating portion of the catheter is located in the proximity of the previously identified site. The catheter then is utilized to accomplish the selected medical procedure. The guidewire may be withdrawn from the vascular system before, during, or after utilization of the catheter.

A typical example of the above process would be to utilize a guidewire to direct an angiographic catheter to a site of a vascular obstruction. Thereafter an angioplasty procedure, e.g., balloon angioplasty, may be carried out by means of, e.g., a balloon angioplasty catheter. Other catheters are designed to perform procedures such as application of ultrasound to an obstruction, delivery of drugs, execution of diagnostic procedures, or any of a number of applications of drugs, energy or other forces within the body.

The present invention is intended to be used with essentially all guidewires. However, guidewires are often coated with a slippery or hydrophilic coating to make the processes of passing a guidewire through a body vessel and passing a catheter over the guidewire proceed more easily. This invention is particularly applicable to the containment, transportation, and dispensing of coated guidewires in the dispenser assembly until they are used in a medical procedure.

The present invention, in a preferred embodiment, is particularly applicable to insertion and utilization of guidewires having predetermined, or preferential distal end configurations other than straight or linear. The distal ends of such guidewires would have a built-in preference, bias, or memory which causes their distal ends to assume (or to resume) a curved, angled, or bent configuration if they are not physically restrained to a straight or linear configuration. For example, some guidewires have what is referred to as a "J" distal end configuration. Guidewires with a "J" distal end configuration, after being inserted into the vasculature in a straight configuration (e.g., held in a linear arrangement by means of a straightener), return to their "J" configuration after the straightening device is withdrawn. When such a guidewire is steered into the vascular system, the rounded bottom of the "J" (as opposed to the tip of the "J") is at the very distal or leading end of the guidewire. In this manner, "J" configuration guidewires present a potentially less traumatic, rounded configuration to the vascular system through which the guidewire passes.

For reasons of device protection, ease of handling and dispensing, and fluid flushing, guidewires tend to be stored and transported in tubular dispenser assemblies, carriers, or containers. Generally speaking, the tubular dispenser assembly or loop of tubing will have a substantially larger inside diameter than the outside diameter of a guidewire contained therein. To utilize a guidewire contained within such an assembly in a medical procedure, the guidewire must be partially and ultimately, totally removed therefrom.

During the transportation and handling of guidewires contained within a shipping or dispenser assembly, a problem has sometimes developed in that guidewires tend to migrate or to emerge from the dispenser in a less than controlled fashion. The guidewire, which may be from 20 to 400 cm in length (or longer), is sufficiently longitudinally rigid so as to have a natural tendency to migrate from its dispenser.

Also, medical personnel handling the guidewire under sterile or near sterile operative conditions must be able to control, as precisely as possible, dispensing of the guidewire. With guidewire handling problems resulting from medical personnel wearing surgical gloves and a guidewire coated with a slippery, hydrophilic coating, exact containment and dispensing of the device can be very important to reducing the duration and increasing the overall success of the medical procedure in which the guidewire is used.

One approach to the above problem has been simply to provide a vinyl, restriction fit cap which fits the open, dispensing end of a tubular guidewire dispenser. This approach has the potential drawback of not being applicable for transportation/storage of guidewires having a so-called "J" distal end. Capped "J" guidewires would require a separate, additional straightener assembly to straighten the "J" guidewire configuration during initial guidewire insertion. In other words, the capped dispenser approach would not likely be applicable to contain guidewires having a non-linear distal end predisposition.

BRIEF SUMMARY OF THE INVENTION

The present invention provides an apparatus and method for containing and dispensing a wire, particularly a guidewire, from a tubular, elongate, or cylindrical transfer, transportation, or carrier assembly e.g., a carrier tube. This invention is particularly useful for containing a coated guidewire within such an assembly.

Briefly, in one aspect, the present invention is an article, device, dispensing collar, or dispensing sleeve. A sleeve of this invention has one end with a smaller overall or effective outside diameter which permits it to be inserted into a tubular wire carrier (while containing a wire therein), the other end having a larger overall, effective or outside diameter or configuration which prevents it from being completely inserted into the same tubular wire carrier. A sleeve of the present invention comprises a substantially cylindrical sleeve body having an axial bore or passage therethrough. The sleeve body has a side wall, an insertion, leading, or first end and a radial stop, restriction, or second end, the bore being of a diameter to permit wire to pass freely or restrictively therethrough. The sleeve body has in its side wall a plurality of slits or openings. The slits, which may be longitudinal or other configuration as viewed from the side, and which may extend partially or completely between the first and second sleeve body ends, pass through the sleeve body side wall so as to divide the sleeve body into sleeve body segments (i.e., transversely to the axis of the sleeve). The integral, i.e., the uncut portions of the sleeve body, and the slits allow the sleeve body segments to be repetitively compressed toward each other (e.g., as the sleeve is inserted into a tube), thereby at least partially collapsing the slits and reducing the diameter of the bore. When the sleeve body segments are compressed toward each other, they restrictively engage a wire passing between them (i.e., through the bore) and thereby permit wire to be contained within and to be controllably dispensed from the tubular container with which the sleeve cooperates.

The sleeve body segments also include lateral or radial projections or rigid fins which are attached thereto or which are molded thereon so as to be part thereof. The lateral projections define the overall, outside, or effective diameter of the portion of the sleeve of which they are a part. The lateral projections project from the sleeve body segments a distance or height so as to cooperate with the inside of a tubular container to compress the sleeve body segments toward each other and at least partially close the slits when the insertion end of the sleeve is inserted into the end of the tubular container. The lateral projections may be disposed between the first and second ends of the sleeve body or they may be located adjacent or proximate to one or the other of said ends. If the lateral projections are not medially disposed, generally speaking, it is preferable that they be molded into the sleeve body adjacent its first end or insertion end. The lateral projections may be fins or bumps and may be longitudinally or transversely disposed with respect to the axis of the sleeve.

The sleeve body further includes radial stop means, e.g., a projecting ring or collar, which prevents the following or second end of the sleeve from entering the tubular carrier when the smaller outside diameter end of the sleeve is inserted therein. Radial stop means are usually molded as part of the sleeve itself. Generally speaking, if the sleeve is to be inserted into the tubular carrier at its insertion end, then the stop means would be located on the opposite, second, restriction, or following end of the sleeve.

In a preferred practice, the present invention includes a guidewire distal end straightener segment integrally molded or continuing from the restriction or second end of the sleeve. The straightener segment has a bore which continues from and is collinear with the bore of the sleeve. For example, a sleeve of this invention may have a conical (to permit ease of insertion of the straightened guidewire) "J" straightener segment extending from the restriction end of the device so as to be integral with the sleeve. In another practice, a sleeve of the present invention can include a fingergrip means, also having a bore, the fingergrip means preferably integrally molded into the second or restriction end of the device so as to be coaxial with the sleeve body bore.

The method of the present invention is one for controllably containing and dispensing wire in or from a tubular container, e.g., a tubular coil, having the wire therein. The method of this invention comprises the steps of: providing a tubular container having a wire therein and having an above-described sleeve in one end thereof with the wire passing therethrough via the bore. The sleeve is located within an end of the tubular container or carrier so that the collar stop means engages the end of the tubular container. Further, the sleeve body segments frictionally engage the wire (via the bore) by virtue of their being compressed toward each other, producing an interference fit between the sleeve body lateral projections and the inside end of the tubular container. The sleeve segments are compressed together because the lateral projections, engaging the inside of the tubular container, are biased toward each other and at least partially close the slits or slots. The frictional engagement between the interior bore of the sleeve body segments and wire substantially restricts or prevents the wire from being pulled from the tubular container.

In the next step of the present method, the sleeve is at least partially pulled from the end of the tubular container so that the lateral projections pass at least partially outside the coil with one end of the sleeve (usually the insertion end) optionally remaining therein. The sleeve body segments separate partially, by at least partially returning to their uncompressed position. This permits the wire to pass restrictively between the sleeve body segments with partial frictional engagement sufficient to prevent unrestricted emergence or migration of the wire from its coil or container assembly.

The last step of the present method involves, alternatively, removing the sleeve from the tubular container so that the sleeve body segments return to their fully separated, uncompressed configuration and permit the wire to be freely dispensed, or reinserting the sleeve into the wire container or dispenser so that the wire is substantially restricted from being dispensed.

In a preferred practice, the method of this invention involves only the two aspects of freely dispensing wire with the sleeve completely removed from the tube or substantially restrictively holding the wire within the tube with the dispenser sleeve inserted into the tube substantially as far as it will go. Utilization of these steps permits enhanced control and deployment of guidewires having very slippery coatings, e.g., Teflon polytetrafluoroethylene, in a medical procedure.

BRIEF DESCRIPTION OF THE DRAWINGS

A better understanding of the present invention as well as other objects and advantages thereof will become apparent upon consideration of the detailed description, especially when taken with the accompanying drawings wherein like numerals designate like parts throughout, and wherein.

DETAILED DESCRIPTION OF THE INVENTION

The present invention is described by specific reference to a guidewire. However, it is to be understood that the present invention can be used to dispense essentially any type of wire contained within a larger diameter carrier. Hence, the specific reference to guidewire should not be construed to narrow the scope of this invention.

Figure 1:
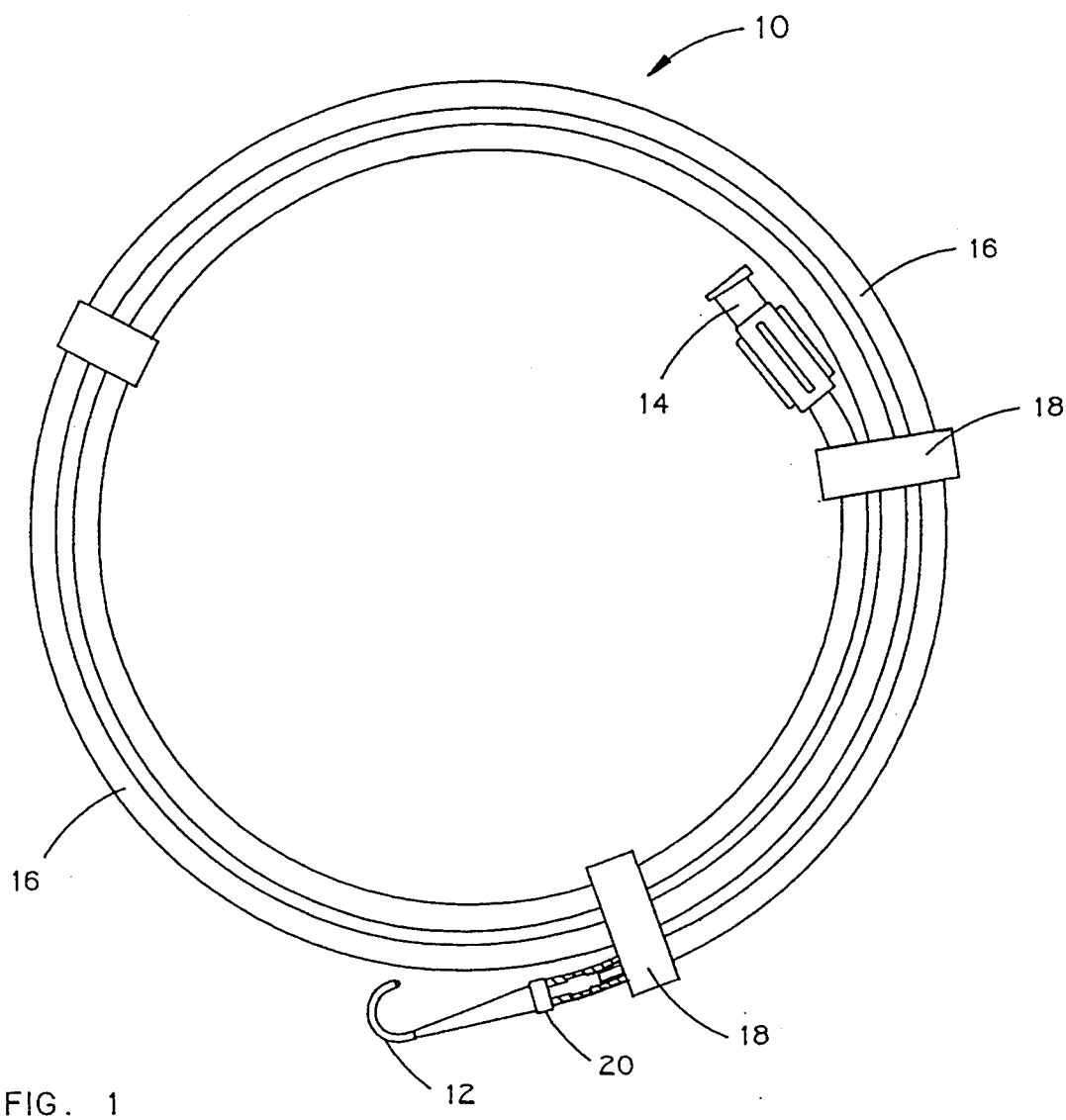
FIG. 1 is a plan view of a guidewire contained within a standard dispenser coil assembly or carrier, the guidewire being retained within the assembly by one embodiment of the present invention.

Thus there is shown, in FIG. 1, a substantially conventional or standard guidewire dispenser assembly or carrier 10. Assembly 10 would be used, for example, to store or to transport a guidewire 12 from the manufacturer to the user. Guidewire dispenser assembly 10 has a substantially larger internal diameter than the outside diameter of guidewire 12. This provides space in which guidewire 12 could be exposed, for example, to treatment media, as desired. As shown, assembly 10 comprises a plurality of loops 16 of a flexible material with separators 18 used to maintain loops 16 in the desired arrangement. The tubular section of assembly 10 would be made from a flexible polymeric material such as, for example, polypropylene. Many thermoplastic, flexible materials may be used to make the tubular section of assembly 10.

Figure 2:
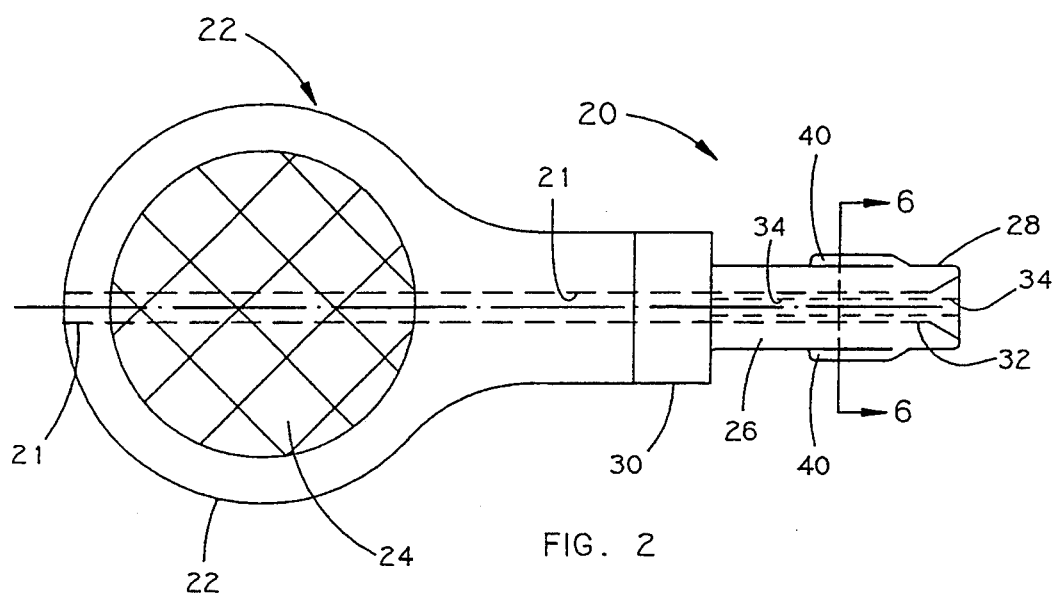
FIG. 2 is a plan view of a dispenser sleeve of the present invention having an optional finger grip.

FIG. 2 shows a dispenser sleeve, device, or keeper 20 of the present invention having an optional finger grip 22. Dispenser sleeve 20, is hollow having a substantially cylindrical hole, bore, or passageway 21 (shown in phantom) therethrough. Bore 21 has a diameter chosen to permit a guidewire to pass freely or controllably (depending upon design considerations) therethrough. Finger grip 22 is a flattened tab having diamond patterned grooves 24 molded or cut therein. Obviously, many other gripping surfaces could be molded into finger grip 22 so as to enhance the user's ability to manipulate the sleeve and thereby contain and control a wire e.g., a guidewire, therein.

Figure 5:
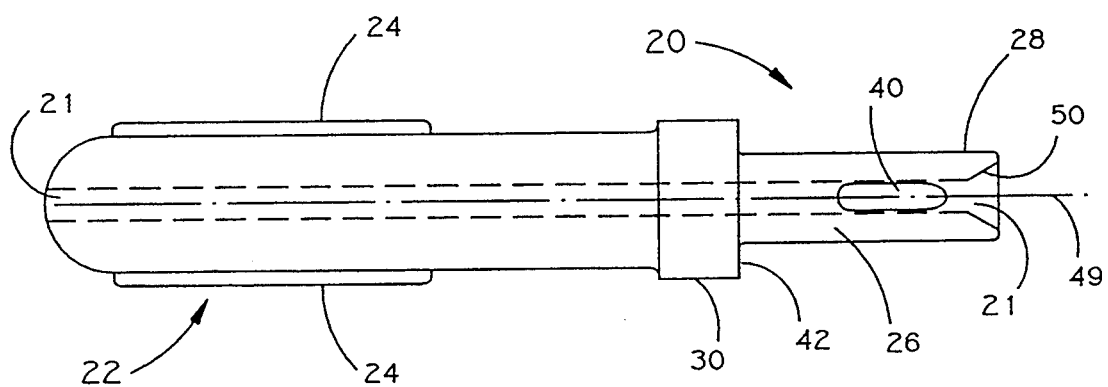
FIG. 5 is a view of the dispenser sleeve of FIG. 2 rotated 90° from the view of FIG. 2.
Figure 6:
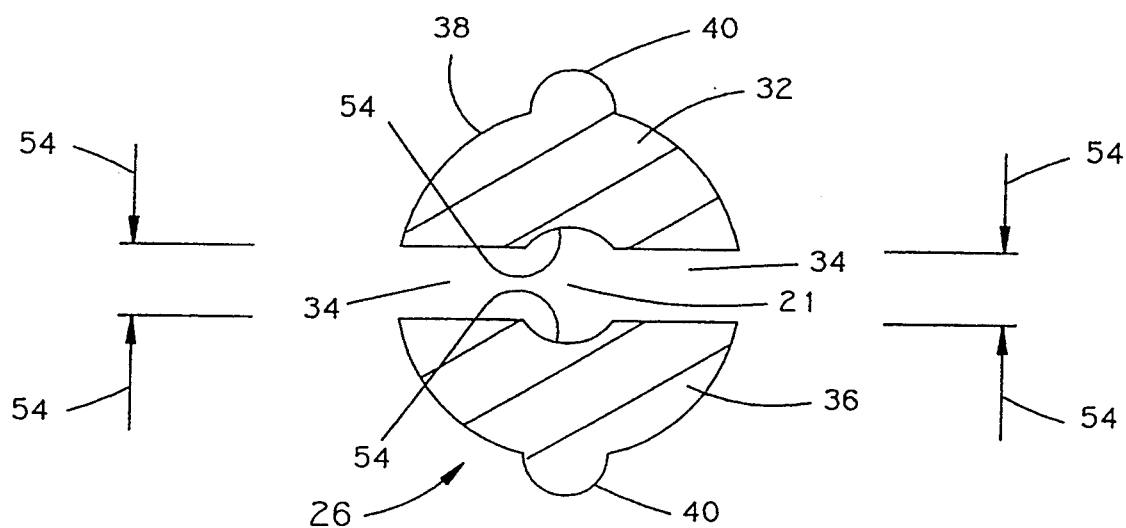
FIG. 6 is a section view of the dispenser sleeve taken along line 6—6 of FIG. 2.
Figure 9:
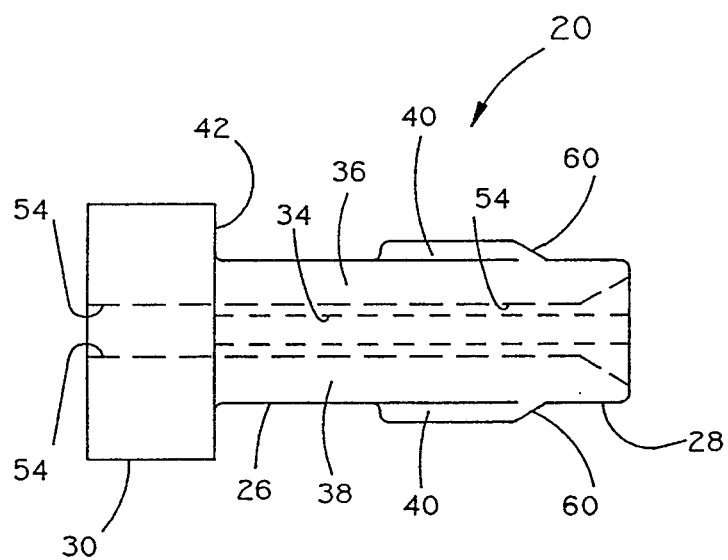
FIGS. 9–11 illustrate further embodiments of the invention.
Figure 10:
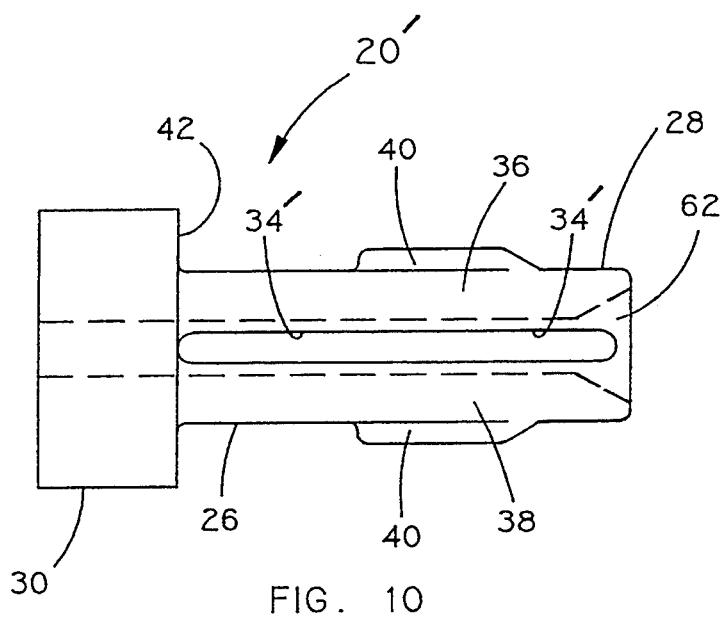
Figure 11:
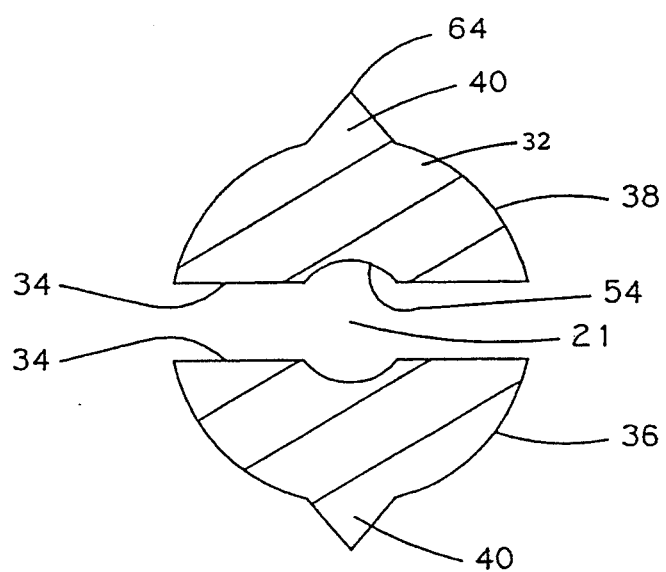

With reference to FIGS. 2, 5, 6, 7, 9, and 10 sleeve 20 comprises a substantially cylindrical, hollow sleeve body 26 having first and second ends 28, 30, respectively, and a sleeve body wall 32. Sleeve body wall 32 is best shown in FIGS. 6 and 11. Sleeve body wall 32 has longitudinally disposed slits 34 which, in this embodiment, run substantially the entire length of sleeve 20 (and therefor sleeve body 26). Slits 34, as best seen in FIG. 6, run completely through side wall 32 so as to divide sleeve body 26 into segments 36, and 38. Slits, cuts, or slots 34 divide dispenser sleeve body 26 into two substantially symmetric halves or segments 36, 38 by dividing sleeve body wall 32 through first sleeve body end 28.

In an alternative embodiment, slits 34 could terminate before reaching first sleeve body end 28 so that both first sleeve body end 28 and second sleeve body end 30 are substantially integral. In essence, this would provide an elongated slot or slit substantially through sleeve body wall 32 with sleeve body segments 36 and 38 being held with respect to each other by side body wall portions therebetween. This variation of the present invention is shown in FIG. 10. Dispenser sleeve 20 further comprises lateral projections 40 and stop means or radial collar 42. Lateral projections 40 are molded into or attached to sleeve body 26 so as to project outside the radius thereof. Stop means 42 may be of any configuration which would prevent sleeve body 26 from completely entering the open end 46 of guidewire dispenser assembly 10. Stop means 42 is located at the restriction or second end of the sleeve and is an integral part thereof.

Figure 3:
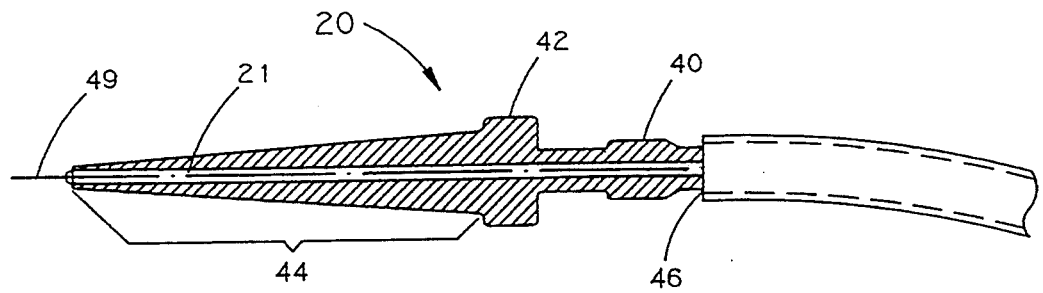
FIG. 3 is a sectional view of an embodiment of the present invention with an optional "J" straightener segment.
Figure 4:
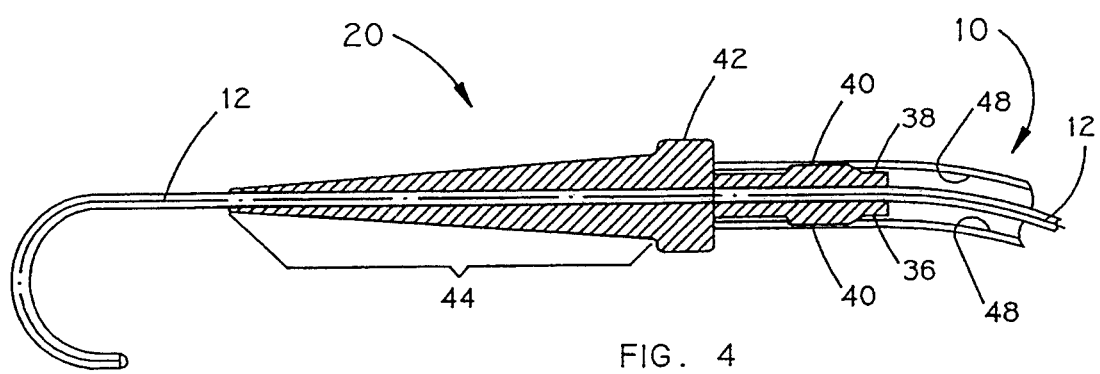
FIG. 4 is a sectional view of the embodiment of the invention shown in FIG. 3 with a "J" configuration guidewire projecting therefrom.
Figure 8:
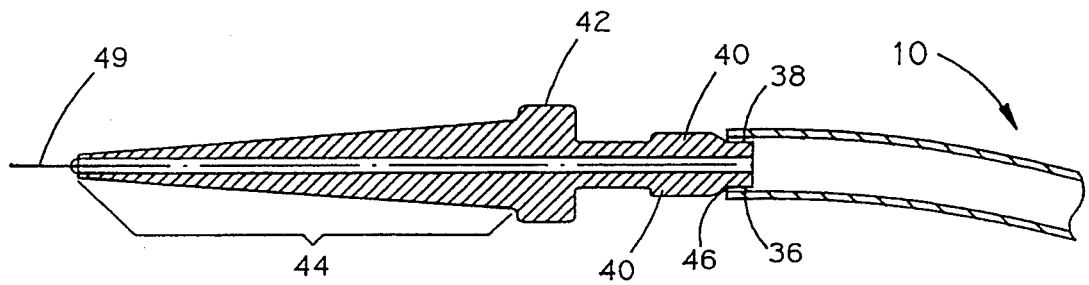
FIG. 8 is a partial sectional view of an embodiment of the invention illustrating partial withdrawal of the sleeve from a guidewire carrier.

FIGS. 3, 4 and 8 illustrate a preferred article of the present invention which further includes a means or segment for straightening the distal end of a guidewire 12 having a predisposition to be curved. In FIGS. 3, 4 and 8, the straightener means or segment is an elongate cone 44. Cone 44, as shown, is molded integrally with the sleeve immediately proximate (or on the end thereof) stop means 42. Elongate cone 44 is tapered away from the second or following end of sleeve 20 to permit the guidewire 12, while straightened, to be inserted into, for example, an introducer needle. The straightening means shown is particularly adapted for straightening a guidewire having a predisposed "J" distal end configuration, as discussed above. The device of FIGS. 3 and 4 is particularly preferred because, in a single integral article, controllable guidewire containment and dispensing are accomplished for a guidewire having a non-linear distal end predisposition. Sleeve 20 shown in FIG. 3 is completely removed from the open end 46 of dispenser assembly 10. Line 49 indicates the axis of the sleeve which is generally collinear with the axis of tubular dispenser assembly 10.

FIG. 4 shows sleeve 20 inserted within the open end 46 of tubular dispenser assembly 10. Sleeve 20 is inserted to the point where collar 42 is substantially in contact with the open end 46 (See, FIG. 3) of dispenser assembly 10. In this manner, sleeve 20 is restricted from further entering assembly 10. As shown in FIG. 4, lateral projections 40 cooperate with the interior wall 48 of assembly 10 to bias sleeve body segments 36, 38 around guidewire 12. Thusly, the guidewire is partially (or completely depending upon the relative dimensions) prevented from migrating or emerging from assembly 10. Longitudinal slit 34 (as shown in FIGS. 2, 6, 7, 10, and 11) would be partially or completely closed as the sleeve body segments are urged or biased toward each other during the insertion process. At the same time, the open end 46 of the guidewire carrier 10 is slightly stretched by lateral projections 40. Some amount of carrier flexibility and collar design adjustment may be needed to obtain the deemed relationship between the sleeve and the open end of the carrier so as to optimally control the wire interaction.

FIG. 5 is a partial view of the dispenser shown in FIG. 2 rotated 90° from the view of FIG. 2. In this illustration, fingergrip 22 is shown to be slightly raised from the remainder of this elongate portion of the device. Fingergrip 22 includes optional diamond patterned grooves 24 (not shown in FIG. 5) which would be molded in a slightly raised portion of the fingergrip. Fingergrip 22 is proximate to and usually is integrally molded at the same time as the rest of dispenser sleeve 20. Shown in phantom in FIG. 5 is passageway or bore 21 which is of a dimension adequate to permit a guidewire to pass therethrough. It should be noted that sleeve bore 21 is interiorly chamfered 50. Chamfer 50 permits a guidewire to be more easily inserted in the first end 28 of sleeve 20.

FIG. 6 has been substantially described above. It also has been noted, in operation, sleeve body segments 36, 38 are biased toward each other as the sleeve 20 is inserted into the open end 46 of assembly 10. FIG. 6, at arrows 52 shows the direction sleeve body segments 36, 38 would be compressed as dispenser sleeve 20 is inserted in the open end 46 of guidewire dispenser assembly 10. Longitudinal slot 34 would tend to be closed, and a wire, particularly a guidewire, within bore 21 would be frictionally engaged by the interior surface 54 which defines bore 21. In this manner, a guidewire within bore 21 would be prevented from accidentally sliding out of assembly 10.

Figure 7:
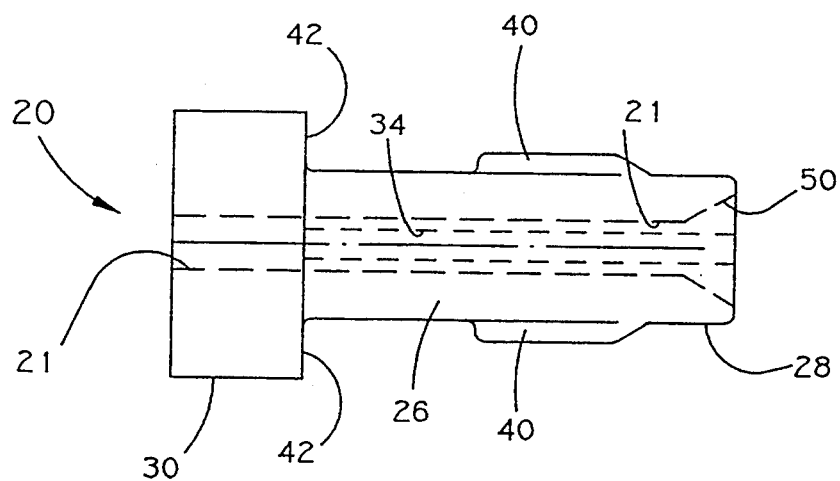
FIG. 7 is a plan view of an embodiment of the present invention with internal detail shown in phantom.

FIG. 7 shows an embodiment of the invention 20 which omits the preferred guidewire straightener and the finger grip. FIG. 7 shows that the diameter of the bore 21 (shown in phantom) may be different from the short dimension of slit 34. Also, slit 34 is shown to divide essentially the entire length of sleeve body 26. Slot or slit 34 may divide less than the entire length of sleeve body 26 and, depending upon design requirements, could divide either or both of first and second ends 28, 30. In other words, slot 34 could be cut so as to project inward from first end 28. Slot 34 may also be simply a notch, a hole (or a series of holes), or a "V"-shaped inward cut opening toward first end 28.

FIG. 8 shows a sleeve of the present invention partially inserted in assembly 10. In this embodiment, lateral projections 40 have been removed from open end 46 of dispenser assembly 10. In this configuration, sleeve body segments 36, and 38 would frictionally engage a guidewire (not shown) and permit it to pass therebetween with some restriction. In this manner, dispensing of guidewire 12 from assembly 10 is controllably achieved. Also in this configuration, sleeve body segments 36, 38 are at least partially disengaged and have returned, in part, to their fully separated position such as that shown in FIG. 6.

A sleeve of the present invention is intended to be used with guidewires having a range of diameters. This is accomplished, in part, by utilization of a tube assembly 10 having considerable elasticity, at least at its open end 46. By virtue of the interaction between projections 40 as they enter open end 46 of a tube, substantial variation in guidewire diameter is permitted. It will be well within the design ability of one skilled in this art to determine the relationship between tube elasticity, and the distance or height projections 40 must extend away from sleeve body 26 to achieve the requisite restrictive fit.

FIG. 9 shows an alternative embodiment in the present invention which would be particularly useful for controllably dispensing the wire from assembly 10. FIG. 9 shows a sleeve of the present invention wherein the leading edge 60 of projections or fins 40 has been ramped toward first end 28. In this manner, partial compression of body segments 36, 38 (in the direction of arrows 52 of FIG. 6) and concomitant partial dispensing of a wire, e.g., by restrictive frictional engagement by interior bore surface 54, may be accomplished.

FIG. 10 shows an alternative embodiment of the present invention wherein slot 34' terminates before it completely divides sleeve body 26. In this alternative embodiment, the undivided or uncut portion of sleeve body 26 between slot 34' and the terminus of first end 28 (indicated at 62) assists the alternative compression and relaxation process which permits controlled delivery or dispensing of a wire from a wire carrier assembly or tube.

It has been found that this embodiment of the invention is particularly easy to load with a guidewire. A guidewire, whether of a bent or straight distal end predisposition, can be easily inserted into the collar from first end 26 because a completely circular bore or hole is presented. In other words, uncut body portion 62 prevent body segments 36, 38 from separating so as to make placement of a wire therebetween difficult. The embodiment of this invention shown in FIG. 10, when constructed with a conical "J" straightener segment, such as that shown at 44 in FIGS. 3, 4, and 8, is a particularly preferred arrangement. A straightener segment or zone would be molded onto or be integral with the second sleeve body 30 to the left of stop means or collar 42.

FIG. 11 shows an alternative embodiment of the device depicted in FIG. 6 wherein projections 40 are pointed 64. The more pointed projections of FIG. 11 (as contrasted with the more rounded profile shown in FIG. 6) allow a slightly more aggressive interaction between sleeve 20 and the open end 46 of the tubular dispenser assembly 10. The above disclosure will suggest many alterations and variations of the present invention to one skilled in this art. All such variations and alterations are to be included within the scope of the attached claims.

What is claimed is:

1. A dispenser sleeve for controllably dispensing a guidewire from within a tubular container, the sleeve comprising:

a substantially cylindrical sleeve body comprising a side wall, and first and second ends, the sleeve body having a bore therethrough, the bore having a diameter which permits wire to pass restrictively therethrough, the sleeve body having in its side wall:

a plurality of slits, the slits extending through said side wall so as to divide the sleeve body into sleeve body segments which can be compressed toward each other by at least partially collapsing the slits, the slits extending from the second end and terminating short of said first end so that said first end defines a completely circular bore hole, the sleeve body segments further including:

lateral projections, the projections being located on the sleeve body segments and projecting therefrom so as to cooperate with the inside of the tubular container to compress the sleeve body segments toward each other into said tubular container thereby engaging a guidewire wire passing between said segments, the sleeve body further including:

stop means located along said second end thereof, said stop means restricting the further entry of said sleeve into said container.

2. A dispenser sleeve according to claim 1 wherein the stop means comprises a radial collar.

3. A dispenser sleeve according to claim 1 which further includes means for straightening the distal end of a guidewire having a predisposition to assume a curved configuration, the means for straightening being located proximate the second end.

4. A dispenser sleeve according to claim 23 wherein the means for straightening is an elongate, conical shape.

5. A dispenser sleeve according to claim 21 which further includes means for straightening the distal end of a guidewire having a predisposition to assume a curved configuration, the means for straightening being located on one side of the stop means, the sleeve body being located on the other.

6. An assembly for dispensing a wire, the assembly comprising a tubular container and a dispensing sleeve, the sleeve comprising:
   a substantially cylindrical sleeve body comprising a side wall, and first and second ends, the sleeve body having a bore therethrough, the bore having a diameter which permits wire to pass therethrough, the sleeve body having in its side wall:
   a plurality of slits, the slits extending through said side wall so as to divide the sleeve body into sleeve body segments which can be compressed toward each other by at least partially collapsing the slits and reducing the diameter of the bore, the slits extending from the second end and terminating short of said first end so that said first end defines a completely circular bore hole, the sleeve body segments further including:
   lateral projections, the projections being located on the sleeve body segments and extending therefrom a distance sufficient to cooperate with the inside of the tubular container to compress the sleeve body segments toward each other to at least partially close the slits when the sleeve is inserted into said tubular container thereby engaging a wire passing between said segments, the sleeve body further including:
   stop means located along said second end thereof, said stop means restricting the entry of said sleeve into said container;
   the tubular container having an open or dispensing end, the interior diameter of the container at its open end and the distance the lateral projections extend away from the sleeve body segments being selected so that wire located between the sleeve body segments can be controllably dispensed from the container by adjustment of the extent to which the sleeve is inserted into the container.

7. An assembly according to claim 6 wherein the tubular container and the dispenser sleeve are adapted to dispense a guidewire.

8. An assembly according to claim 7 wherein the guidewire has a distal end predisposition other than linear.

9. An assembly according to claim 8 wherein the dispenser sleeve further includes a straightener segment for straightening the distal end of the guidewire, the straightener segment having a bore therethrough which is collinear with the bore of said sleeve and is attached or integral with the second end thereof.

* * * * *